US010441446B2

(12) United States Patent
Rowe et al.

(10) Patent No.: US 10,441,446 B2
(45) Date of Patent: Oct. 15, 2019

(54) ENDOLUMINAL PROSTHESES INCLUDING MULTIPLE HELICAL WIRES

(71) Applicant: Medtronic Vascular, Inc., Santa Rosa, CA (US)

(72) Inventors: Travis Rowe, Santa Rosa, CA (US); Gustaf Belt, Santa Rosa, CA (US)

(73) Assignee: Medtronic Vascular, Inc., Santa Rossa, CA (US)

( * ) Notice: Subject to any disclaimer, the term of this patent is extended or adjusted under 35 U.S.C. 154(b) by 44 days.

(21) Appl. No.: 15/692,160

(22) Filed: Aug. 31, 2017

(65) Prior Publication Data
US 2019/0060092 A1 Feb. 28, 2019

(51) Int. Cl.
| | |
|---|---|
| *A61F 2/07* | (2013.01) |
| *A61F 2/88* | (2006.01) |
| *A61F 2/915* | (2013.01) |
| *A61F 2/91* | (2013.01) |
| *A61F 2/89* | (2013.01) |
| *A61F 2/82* | (2013.01) |

(52) U.S. Cl.
CPC .............. *A61F 2/88* (2013.01); *A61F 2/07* (2013.01); *A61F 2/91* (2013.01); *A61F 2/915* (2013.01); *A61F 2/89* (2013.01); *A61F 2002/828* (2013.01); *A61F 2002/91525* (2013.01); *A61F 2220/0058* (2013.01); *A61F 2230/0054* (2013.01); *A61F 2230/0091* (2013.01); *A61F 2250/006* (2013.01)

(58) Field of Classification Search
CPC ........................................................ A61F 2/88
See application file for complete search history.

(56) References Cited

U.S. PATENT DOCUMENTS

| | | | | |
|---|---|---|---|---|
| 4,886,062 A | * | 12/1989 | Wiktor | A61F 2/88 606/194 |
| 5,749,919 A | * | 5/1998 | Blanc | A61F 2/88 606/194 |

(Continued)

FOREIGN PATENT DOCUMENTS

| | | |
|---|---|---|
| EP | 3087957 A1 | 11/2016 |
| JP | 2004-033579 A | 2/2004 |

OTHER PUBLICATIONS

Notification of Transmittal of the International Search Report and the Written Opinion of the Searching Authority, or the Declaration issued in International Application No. PCT/US2018/045721, dated Nov. 19, 2018.

*Primary Examiner* — Megan Y Wolf

(57) ABSTRACT

A prosthesis includes a first wire bent into a first waveform and spirally wrapped into a first helix having a plurality of windings that form a hollow cylindrical shape and a second wire bent into a second waveform and spirally wrapped into a second helix having a plurality of windings that form a hollow cylindrical shape. The first and second wires are disposed relative to each other such that the plurality of windings of the first wire and the plurality of windings of the second wire are disposed about a common longitudinal axis and the plurality of windings of the first wire and the plurality of windings of the second wire are axially offset from each other, with windings of the plurality of windings of the first wire alternating or interwoven between windings of the plurality of windings of the second wire along a length of the prosthesis.

16 Claims, 5 Drawing Sheets

(56) References Cited

U.S. PATENT DOCUMENTS

| | | | |
|---|---|---|---|
| 6,019,779 A * | 2/2000 | Thorud | A61F 2/88 |
| | | | 606/198 |
| 6,042,597 A | 3/2000 | Kveen et al. | |
| 6,423,091 B1 | 7/2002 | Hojeibane | |
| 7,942,917 B2 | 5/2011 | Nowark, Jr. | |
| 8,226,705 B2 | 7/2012 | Griswold | |
| 8,366,765 B2 | 2/2013 | Baldwin et al. | |
| 8,801,775 B2 | 8/2014 | Griswold | |
| 8,998,975 B2 | 4/2015 | Rowe | |
| 9,060,889 B2 | 6/2015 | Bliss et al. | |
| 9,421,601 B2 | 8/2016 | Bliss et al. | |
| 2007/0219618 A1 * | 9/2007 | Cully | A61F 2/88 |
| | | | 623/1.13 |
| 2007/0250148 A1 * | 10/2007 | Perry, Jr. | A61F 2/91 |
| | | | 623/1.11 |
| 2010/0249904 A1 * | 9/2010 | Takayuki | A61F 2/91 |
| | | | 623/1.16 |
| 2011/0184506 A1 * | 7/2011 | Igaki | A61F 2/90 |
| | | | 623/1.16 |
| 2013/0204343 A1 | 8/2013 | Shalev | |

\* cited by examiner

ENDOLUMINAL PROSTHESES INCLUDING MULTIPLE HELICAL WIRES

FIELD OF THE INVENTION

This invention generally relates to endoluminal prostheses. More specifically, the invention relates to endoluminal prostheses including at least two helical wires.

BACKGROUND OF THE INVENTION

A stent is a type of endoluminal prosthesis. Stents are generally tubular open-ended structures providing support for damaged, collapsing, or occluded blood vessels. They are radially expandable from a radially compressed configuration for delivery to the affected vessel site to a radially expanded configuration when deployed at the affected vessel treatment site, with the radially expanded configuration having a larger diameter than the radially compressed configuration. Stents are flexible, which allows them to be inserted through, and conform to, tortuous pathways in the blood vessels. Stents are generally inserted in the radially compressed configuration and expanded to the radially expanded configuration either through a self-expanding mechanism, or through the use of a balloon catheter.

A graft is another type of endoluminal prosthesis, which is used to repair and replace various body vessels. Whereas the stent provides structural support to hold a damaged vessel open, a graft provides an artificial lumen through which blood may flow. Grafts are tubular devices that may be formed of a variety of materials including textile, and non-textile materials.

Stents and graft may be combined to form a stent-graft prosthesis, providing both structural support and an artificial lumen through which blood may flow. A stent-graft prosthesis is particularly useful to isolate aneurysms or other blood vessel abnormalities from normal blood pressure, reducing pressure on the weakened vessel wall, thereby reducing the chance of vessel rupture while maintaining blood flow. A stent-graft prosthesis is placed within the aneurysmal blood vessel to create a new flow path and an artificial flow conduit through the aneurysm, thereby reducing the exertion of blood pressure on the aneurysm. The stent-graft prosthesis incorporates one or more radially expandable stent(s) to be radially expanded in situ to anchor the tubular graft to the wall of the blood vessel at sites upstream and downstream of the aneurysm. Thus, endovascular stent-graft prostheses are typically held in place by mechanical engagement and friction by the outward radial force imparted on the wall of the blood vessel by the self-expanding or balloon expandable stent(s).

The design of a stent-graft prosthesis must balance strength and flexibility. Generally, increasing the strength a stent-graft prosthesis reduces its flexibility. Conversely, increasing the flexibility of stent-graft prosthesis generally decreases its strength. For example, a stent-graft prosthesis formed with a single helical wire is generally highly flexible but the single helical wire generally provides little support or strength when the stent-graft prosthesis is under compression. More particularly, the single helical wire has the potential to collapse under local compression that may be caused by plaque in peripheral vessels or caused by other prostheses in aortic parallel or chimney applications. Damage or malfunctioning of any portion of the single helical wire along the length of the stent-graft prosthesis cause the entirety of the stent-graft prosthesis to fail, as there are no failsafe or backup support structures on a stent-graft prosthesis formed by a single helical wire.

Accordingly, there is a need for an improved stent-graft prosthesis having additional strength and redundant structure while maintaining flexibility.

BRIEF SUMMARY OF THE INVENTION

Embodiments hereof are directed to a prosthesis including a first wire bent into a first waveform and spirally wrapped into a first helix having a plurality of windings that form a hollow cylindrical shape and a second wire bent into a second waveform and spirally wrapped into a second helix having a plurality of windings that form a hollow cylindrical shape. The first and second wires are disposed relative to each other such that the plurality of windings of the first wire and the plurality of windings of the second wire are disposed about a common longitudinal axis and the plurality of windings of the first wire and the plurality of windings of the second wire are axially offset from each other, with windings of the plurality of windings of the first wire interwoven between windings of the plurality of windings of the second wire along a length of the prosthesis.

Embodiments hereof are directed to a stent-graft prosthesis including a tubular graft, a first wire and a second wire. The first wire is bent into a first waveform and is spirally wrapped into a first helix having a plurality of windings that form a hollow cylindrical shape. The first wire has opposing first and second ends and a midportion extending therebetween, and the first wire is coupled to the tubular graft. The second wire is bent into a second waveform and is spirally wrapped into a second helix having a plurality of windings that form a hollow cylindrical shape. The second wire has opposing first and second ends and a midportion extending therebetween, and the second wire is coupled to the tubular graft. The first and second wires are disposed relative to each other such that the plurality of windings of the first wire and the plurality of windings of the second wire are disposed about a common longitudinal axis and the plurality of windings of the first wire and the plurality of windings of the second wire are axially offset from each other, with windings of the plurality of windings of the first wire interwoven between windings of the plurality of windings of the second wire along a length of the stent-graft prosthesis. The first and second wires are not coupled to each other along the midportions thereof except through the tubular graft.

Embodiments hereof are directed to a stent-graft prosthesis including a tubular graft, a first wire, a second wire, and a third wire. The first wire is bent into a first waveform and is spirally wrapped into a first helix having a plurality of windings that form a hollow cylindrical shape. The first wire has opposing first and second ends and a midportion extending therebetween, and the first wire is coupled to the tubular graft. The second wire is bent into a second waveform and is spirally wrapped into a second helix having a plurality of windings that form a hollow cylindrical shape. The second wire has opposing first and second ends and a midportion extending therebetween, and the second wire is coupled to the tubular graft. The third wire is bent into a third waveform and is spirally wrapped into a third helix having a plurality of windings that form a hollow cylindrical shape. The third wire has opposing first and second ends and a midportion extending therebetween, and the third wire is coupled to the tubular graft. The first, second, and third wires are disposed relative to each other such that the plurality of windings of each of the first, second, and third wires are disposed about a common longitudinal axis and the plurality of windings of each of the first, second, and third wires are axially offset to each other, with windings of the pluralities of windings of the first, second, and third wires interwoven between each other along a length of the stent-graft prosthesis. The first, second, and third wires are not coupled to each other along the midportions thereof except through the tubular graft.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. Unless otherwise indicated, the term "self-expanding" is used in the following description with reference to one or more stent structures of the prostheses hereof and is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

The following detailed description is merely exemplary in nature and is not intended to limit the invention or the application and uses of the invention. Although the description of the invention is in the context of treatment of blood vessels, the invention may also be used in any other body passageways where it is deemed useful. Furthermore, there is no intention to be bound by any expressed or implied theory presented in the preceding technical field, background, brief summary or the following detailed description.

Figures 1, 1A:
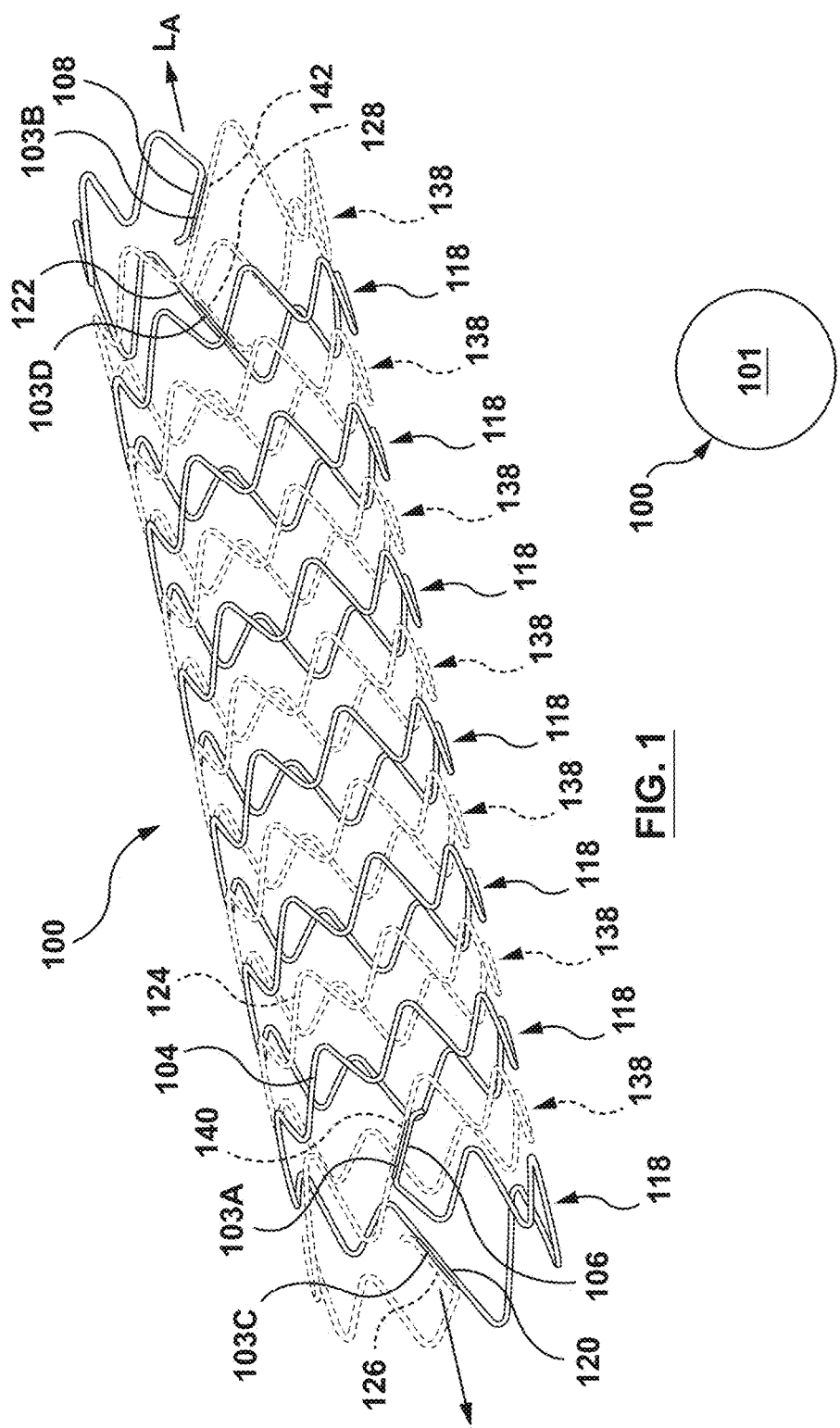
FIG. 1 is a perspective view of a stent prosthesis according to an embodiment hereof, wherein the stent prosthesis includes a first wire bent into a first waveform and spirally wrapped into a first helix having a plurality of windings and a second wire bent into a second waveform and spirally wrapped into a second helix having a plurality of windings.
FIG. 1A is an end view of the stent prosthesis of FIG. 1.

FIG. 1 is a perspective view of a stent prosthesis 100 according to an embodiment hereof. Stent prosthesis 100 includes a radially compressed configuration (not shown) for delivery to the affected site of a blood vessel and a radially expanded configuration when deployed, which is shown in FIG. 1. Stent prosthesis 100 is a generally tubular, open-ended structure that defines a lumen 101 (see end view of FIG. 1A) therethrough. Stent prosthesis 100 may be self-expanding or balloon expandable. Stent prosthesis 100 includes a first wire 104 and a second wire 124, which will be described herein in turn with respect to FIGS. 2 and 3, respectively. In FIGS. 1 and 3, second wire 124 is shown with dotted lines for sake of illustration only in order to distinguish first and second wires 104, 124 from each other.

Figure 2:
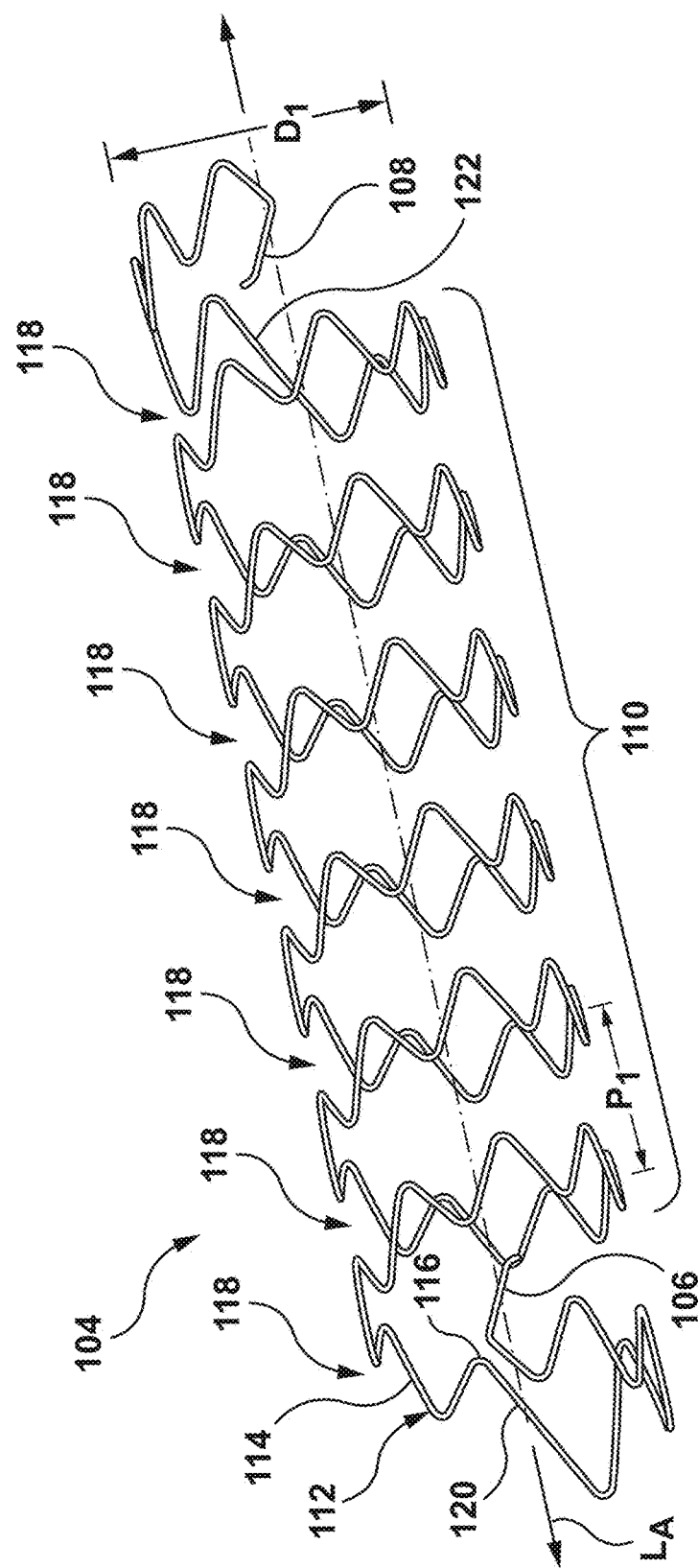
FIG. 2 is a perspective view of the first wire of FIG. 1, removed from the stent prosthesis for illustrative purposes only.
Figure 3:
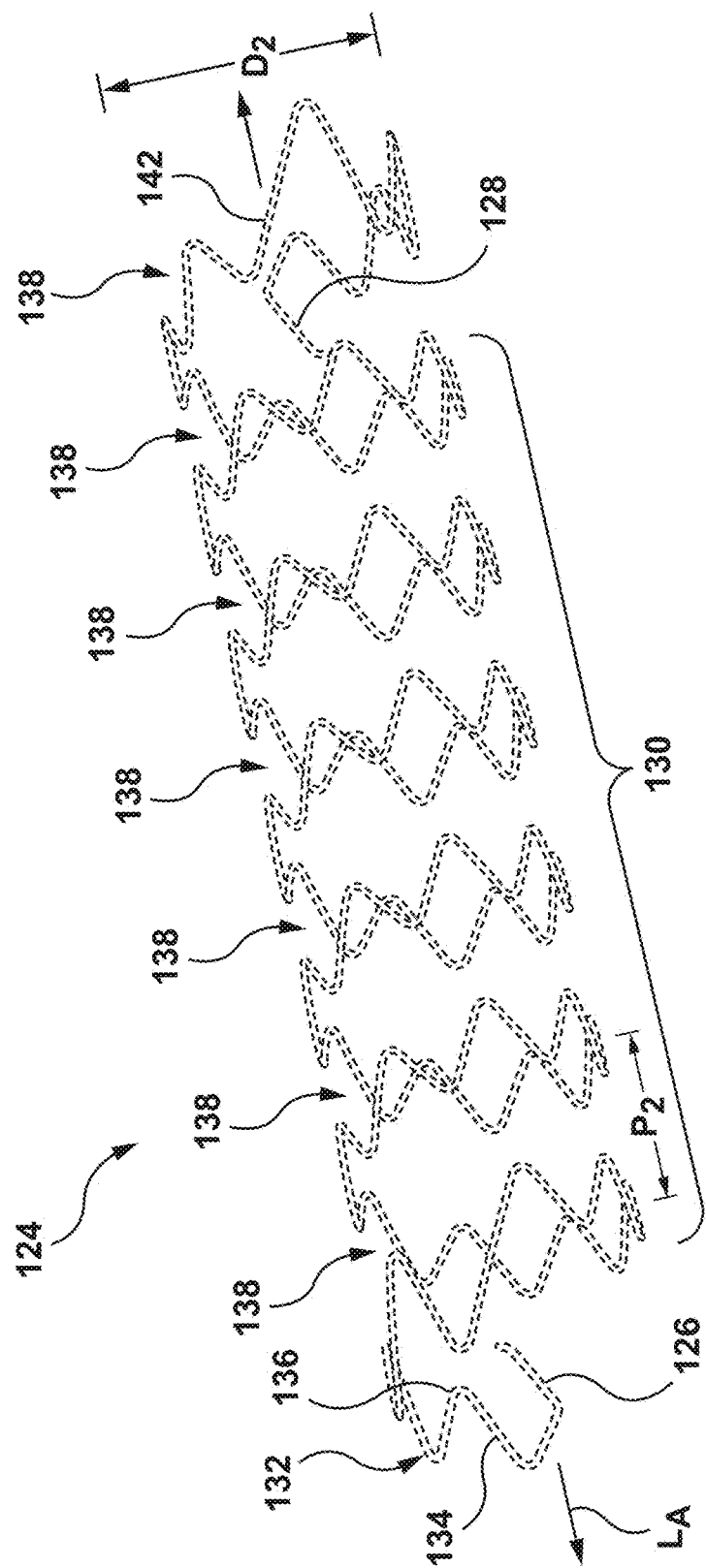
FIG. 3 is a perspective view of the second wire of FIG. 1, removed from the stent prosthesis for illustrative purposes only.

FIG. 2 is a perspective view of first wire 104 removed from stent prosthesis 100 for illustrative purposes only. First wire 104 is a continuous element or strand that has a first end 106, an opposing second end 108, and a midportion 110 extending therebetween. First wire 104 is bent into a first waveform 112 and is spirally wrapped into a first helix having a plurality of bands or windings 118 that form a hollow cylindrical shape. More particularly, first waveform 112 has a generally sinusoidal pattern or configuration including a plurality of crowns or bends 116 and a plurality of struts or straight segments 114 with each crown being formed between a pair of opposing struts. Except as otherwise described herein, the series of struts 114 and crowns 116 have a consistent or non-varying distance between the crowns 116, thereby providing a generally sinusoidal waveform. First wire 104 bent into first waveform 112 is then helically or spirally wrapped into a tubular or hollow cylindrical shape. First wire 104 may also be referred to herein as a helical wire after it has been helically or spirally wrapped into a tubular or hollow cylindrical shape. More particularly, first wire 104 is spirally wrapped into a first helix that includes the plurality of windings 118 disposed about a longitudinal axis $L_A$. As used herein, a band or winding refers to one complete helix turn or revolution of a helix. In an embodiment hereof, each winding 118 has a pitch $P_1$ (the axial distance of a single winding) and a diameter $D_1$. Although first wire 104 is shown with seven windings 118 in FIGS. 1 and 2, it will be understood by one of ordinary skill in the art that first wire 104 may include a greater or smaller number of windings depending upon the desired length of stent prosthesis 100 and/or the intended application thereof. During manufacture thereof, first wire 104 is spirally wrapped onto a mandrel (not shown) or can formed by machining, etching, and the like to assume the above-described configuration.

FIG. 3 is a perspective view of second wire 124 removed from stent prosthesis 100 for illustrative purposes only.

Second wire 124 is similar in construction to first wire 104, except for the positioning or placement of elongated struts 140, 142 which are described in more detail herein. Similar to first wire 104, second wire 124 is a continuous element or strand that has a first end 126, an opposing second end 128, and a midportion 130 extending therebetween. Second wire 124 is bent into a second waveform 132 and is spirally wrapped into a second helix having a plurality of bands or windings 138 that form a hollow cylindrical shape. More particularly, second waveform 132 has a generally sinusoidal pattern or configuration including a plurality of crowns or bends 136 and a plurality of struts or straight segments 134 with each crown being formed between a pair of opposing struts. Except as otherwise described herein, the series of struts 134 and crowns 136 have a consistent distance between the crowns 136, thereby providing a generally sinusoidal waveform. Second wire 124 bent into second waveform 132 is then helically or spirally wrapped into a tubular or hollow cylindrical shape. Second wire 124 may also be referred to herein as a helical wire after it has been helically or spirally wrapped into a tubular or hollow cylindrical shape. More particularly, second wire 124 is spirally wrapped into a second helix that includes the plurality of windings 138 disposed about longitudinal axis $L_A$. In an embodiment hereof, each winding 138 has a pitch $P_2$ and a diameter $D_2$. In an embodiment, pitch $P_2$ of the second helix of second wire 124 is equal to or the same as pitch $P_1$ of the first helix of first wire 104. In addition, in an embodiment hereof, diameter $D_2$ of the second helix of second wire 124 is equal to or the same as diameter $D_1$ of the first helix of first wire 104. Thus, as shown in the embodiment of FIGS. 1-3, the first and second helices of first and second wires 104, 124, respectively, are of the same size and pitch and are disposed about common longitudinal axis $L_A$. Although second wire 124 is shown with seven windings 138 in FIGS. 1 and 3, it will be understood by one of ordinary skill in the art that second wire 124 may include a greater or smaller number of windings depending upon the desired length of stent prosthesis 100 and/or the intended application thereof. During manufacture thereof, second wire 124 is spirally wrapped onto a mandrel (not shown) or can formed by machining, etching, and the like to assume the above-described configuration.

When stent prosthesis 100 is self-expanding, first and second wires 104, 124 may be formed from any suitable self-expanding material including but not limited to nickel titanium, Nitinol, nickel-cobalt-chromium-molybdenum (MP35N), stainless steel, high spring temper steel, or any other metal or composite having elastic properties to permit extension and recoil suitable for purposes of the present disclosure. In another embodiment hereof, stent prosthesis 100 may be balloon expandable and first and second wires 104, 124 may be formed from any suitable material for providing artificial radial support to the wall tissue, including but not limited to stainless steel, nickel-titanium (nitinol), nickel-cobalt alloy such as MP35N, cobalt-chromium, tantalum, titanium, a polymeric material, platinum, gold, silver, palladium, iridium, and the like.

First and second wires 104, 124 are disposed relative to each other such that the plurality of windings 118 of first wire 104 and the plurality of windings 138 of second wire 124 are disposed about a common longitudinal axis, i.e., longitudinal axis $L_A$, and the plurality of windings 118 of first wire 104 and the plurality of windings 138 of second wire 124 are axially offset from each other. First wire 104 and second wire 124 are axially offset from each other by being spirally wrapped at differing starting points into a hollow cylindrical shape. "Axially offset" as used herein means that the plurality of windings 118 of first wire 104 are longitudinally shifted a predetermined amount or distance relative to the plurality of windings 138 of second wire 124. Windings 118 of first wire 104 alternate between windings 138 of second wire 124 such that windings 118, 138 of first and second wires 104, 124, respectively, occur in or form a repeating alternating series or pattern. Stated another way, windings 118 of first wire 104 are intertwined, interlaced, or interwoven with windings 138 of second wire 124 such that along midportions 110, 130 of first and second wires 104, 124, respectively, a single winding 118 of the first helix (formed by first wire 104) is disposed between two adjacent windings 138 of the second helix (formed by second wire 124). Further, a single winding 138 of the second helix is disposed between two adjacent windings 118 of the first helix. In an embodiment, the predetermined amount of distance of the axial offset of the plurality of windings 118 of first wire 104 is equal to half of the pitch ($P_2$) of the second helix formed by second wire 124 such that a single winding 118 is disposed mid-way between two adjacent windings 138 of the second helix formed by second wire 124. The uniform or consistent spacing between alternating windings 118, 138 of first and second wires 104, 124, respectively, permit stent prosthesis 100 to expand evenly.

Providing stent prosthesis 100 with both first and second wires 104, 124 (as opposed to a single wire) offers kink resistance, additional flexibility, and improved resistance to local compression of stent prosthesis 100. More particularly, due to the axial offset of first and second wires 104, 124, stent prosthesis 100 has improved or greater strength and thus is less likely to collapse under local compression that may be caused by plaque in peripheral vessels. In addition, stent prosthesis 100 having improved or greater strength is less likely to collapse under local compression that may be caused by other prostheses in aortic parallel or chimney applications. Thus, stent prosthesis 100 may be particularly advantageous when used as a branch vessel prosthesis that is configured to be deployed in parallel with a main vessel prosthesis. For example, depending on the region of the aorta involved, an aneurysm may extend into segments of the aorta from which smaller branch arteries extend. When branch vessel and main vessel prostheses are deployed together, the branch vessel prostheses can direct blood from the main vessel into the branch vessel using a "snorkel" or "chimney" technique for endovascular aortic aneurysm repair. The branch vessel prosthesis is implanted within the branch vessel and follows a path within the aorta that is parallel to the main vessel prosthesis. The branch vessel prosthesis creates a flow channel that runs between the main vessel prosthesis and the aortic wall, thereby preserving or restoring branch-vessel blood flow.

Midportion 110 of first wire 104 is not directly coupled to midportion 130 of second wire 124. Stated another way, first and second wires 104, 124 are independent or separate from each other and are not attached to each other along midportions 110, 130 thereof. As such, adjacent windings 118, 138 within midportions 110, 130 of first and second wires 104, 124 are permitted to flex or bend independently from one another and therefore maintain the structural integrity of stent prosthesis 100 as a whole in the event of a collapse of one of first or second wires 104, 124 under local compression that may be caused by plaque in peripheral vessels or caused by other prostheses in aortic parallel or chimney applications. Thus, the potential collapse of one of first or second wires 104, 124 does not result in the failure of stent prosthesis 100 entirely.

However, although first and second wires 104, 124 are independent or separate from each other along midportions 110, 130 thereof, the free ends of first wire 104 are attached to second wire 124 and the free ends of second wire 124 are attached to first wire 104 in order to provide additional strength and stability to stent prosthesis 100. More particularly, in an embodiment hereof which is shown in FIG. 1, first end 106 of first wire 104 is attached or secured to a first elongated strut 140 of second wire 124 via a weld 103A or connector (not shown) and second end 108 of first wire 104 is attached or secured to a second elongated strut 142 of second wire 124 via a weld 103B or connector (not shown). In an embodiment, first elongated strut 140 and second elongated strut 142 are disposed at opposing end portions of second wire 124. Similarly, first end 126 of second wire 124 is attached or secured to a first elongated strut 120 of first wire 104 via a weld 103C or connector (not shown) and second end 128 of second wire 124 is attached or secured to a second elongated strut 122 of first wire 104 via a weld 103D or connector (not shown). In an embodiment, first elongated strut 120 and second elongated strut 122 are disposed at opposing end portions of first wire 104. As used herein, "elongated strut" means a strut that has a longer length compared to the vast majority of struts of the respective waveform. Thus, elongated struts 140, 142 of second wire 124 are configured to have a relatively longer length than standard struts 134 of second waveform 132 and elongated struts 120, 122 of first wire 104 are configured to have a relatively longer length than standard struts 114 of first waveform 112. Utilization of elongated struts as an attachment point between first and second wires 104, 124, is beneficial because such elongated struts permit longer lengths of welds 103A, 103B, 103C, 103D. Longer welds ensure that the structural strength of stent prosthesis 100 is not adversely compromised. More particularly, in an embodiment hereof first and second wires 104, 124 are each formed from a superelastic material such as but not limited to Nitinol. The structural characteristics of a component formed from a superelastic material is dependent on the composition of the material. Joining two components formed from a superelastic material (i.e., first and second wires 104, 124) by welding alters the composition of the material and commonly negates the superelastic nature of the material. For this reason, welds are commonly positioned in regions of lower stress and strain of a stent prosthesis. However, even in regions of lower stress and strain, it is advantageous to weld regions of larger geometry than the superelastic region. In an embodiment, the length of each weld 103A, 103B, 103C, 103D may be four times the diameter of first or second wires 104, 124. Loading on the smaller superelastic region (i.e., the cross-section of each of first and second wires 104, 124) is balanced or spread out by the larger welded region so that the structural strength of stent prosthesis 100 is not compromised. Although benefits of utilizing elongated struts as an attachment point between first and second wires 104, 124 are described above with respect to welds 103A, 103B, 103C, 103D, alternative methods of joining first and second wires 104, 124 also benefit from utilizing elongated struts as an attachment point. For example, elongated struts provide sufficient space or length for first and second wires 104, 124 to be joined together by a crimp tube rather than a weld.

However, although struts 140, 142, 120, 122 are illustrated and described as elongated, in another embodiment hereof these struts may have a length equal to the length of other struts of the respective waveform and thus are not required to be elongated as described above. In addition, although first and second wires 104, 124 are illustrated and described with only struts 140, 142, 120, 122 as being elongated compared to the vast majority of struts of first and second waveforms 112, 132, in another embodiment hereof additional struts of first and second waveforms 112, 132, may alternatively and/or additionally be elongated. Further, although such additional elongated struts are not required to be utilized in an attachment point between first and second wires 104, 124, such additional elongated struts may be utilized in the formation of additional attachments points between first and second wires 104, 124 in order to provide further strength and stability to stent prosthesis 100. For example, in an embodiment hereof, additional attachments points between first and second wires 104, 124 may be desired along midportions 100, 130 thereof when stent prosthesis 100 is a relatively longer prosthesis. As the length-diameter aspect ratio of stent prosthesis 100 increases, additional attachment points between first and second wires 104, 124 may be desired along midportions 100, 130 thereof.

Figure 4:
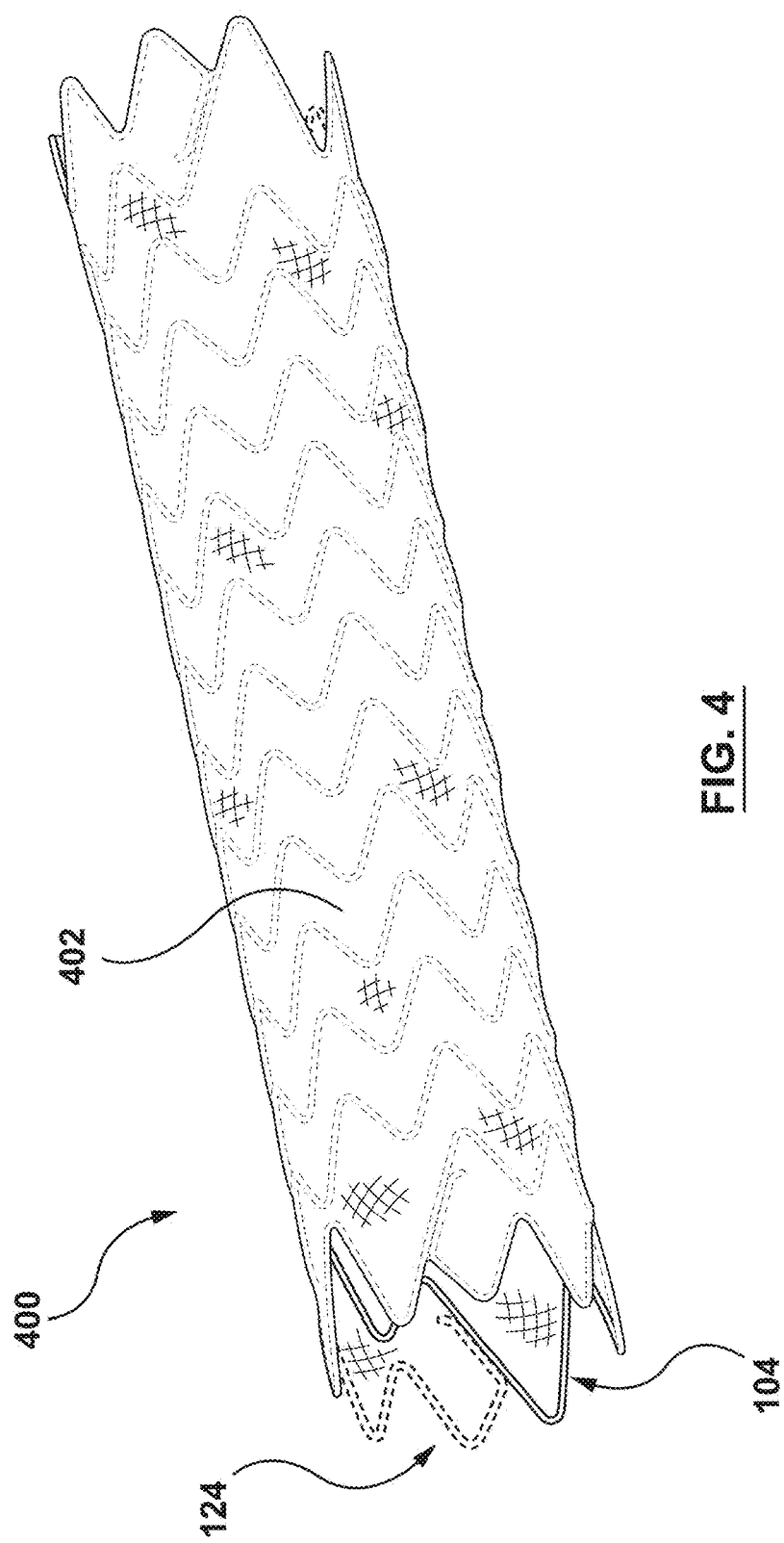
FIG. 4 is a perspective view of a stent-graft prosthesis according to an embodiment hereof, wherein the stent-graft prosthesis includes a tubular graft, a first wire bent into a first waveform and spirally wrapped into a first helix having a plurality of windings and a second wire bent into a second waveform and spirally wrapped into a second helix having a plurality of windings.

Although FIG. 1 illustrates a stent prosthesis having only first and second wires 104, 124, it will be understood by one of ordinary skill in the art that first and second wires 104, 124 may be used to form a stent-graft prosthesis. More particularly, FIG. 4 illustrates a stent-graft prosthesis 400 that includes a tubular graft 402 and first and second wires 104, 124 which are each coupled to tubular graft 402. First and second wires 104, 124 may be coupled to tubular graft 402 using stitching or other means known to those of skill in the art. In the embodiment shown in FIG. 4, first and second wires 104, 124 are coupled to an inner surface of tubular graft 402. However, first and second wires 104, 124 may alternatively be coupled to an outer surface of tubular graft 402.

Tubular graft 402 may be any suitable graft material, for example and not limited to, woven polyester, DACRON® material, expanded polytetrafluoroethylene, polyurethane, silicone, or other suitable materials. In another embodiment, the graft material could also be a natural material such as pericardium or another membranous tissue such as intestinal submucosa. When stent-graft prosthesis 400 is used for treating an aneurysm, first and second wires 104, 124 have sufficient radial spring force and flexibility to conformingly engage tubular graft 402 with the body lumen inner wall, to avoid excessive leakage, and prevent pressurization of the aneurysm, i.e., to provide a leak-resistant seal. Although some leakage of blood or other body fluid may occur into the aneurysm isolated by stent-graft prosthesis 400, an optimal seal will reduce the chances of aneurysm pressurization and resulting rupture. In addition to the sealing aspect, first and second wires 104, 124 have sufficient radial spring force to maintain patency of stent-graft prosthesis 400 in order to allow for unobstructed blood flow there-through.

As described above, first and second wires 104, 124 are independent or separate from each other and are not attached to each other at least along midportions 110, 130 thereof. However, first and second wires 104, 124 are connected or indirectly linked to each other along midportions 110, 130 thereof via graft material of tubular graft 402 that extends therebetween. Stated another way, first and second wires 104, 124 are not coupled to each other along midportions 110, 130 thereof except through tubular graft 402. Further, as described above, in the embodiment of FIG. 4, first and second ends 106, 108, respectively, of first wire 104 are attached to second wire 124 and first and second ends 126, 128, respectively, of second wire 124 are attached to first wire 104 in order to provide additional strength and stability to stent prosthesis 100. However, due to the securement of first and second wires 104, 124 to tubular graft 402, first and second ends 106, 108, respectively, of first wire 104 are not required to be attached or secured to second wire 124 and first and second ends 126, 128, respectively, of second wire 124 are not required to be attached or secured to first wire 104.

Figure 5:
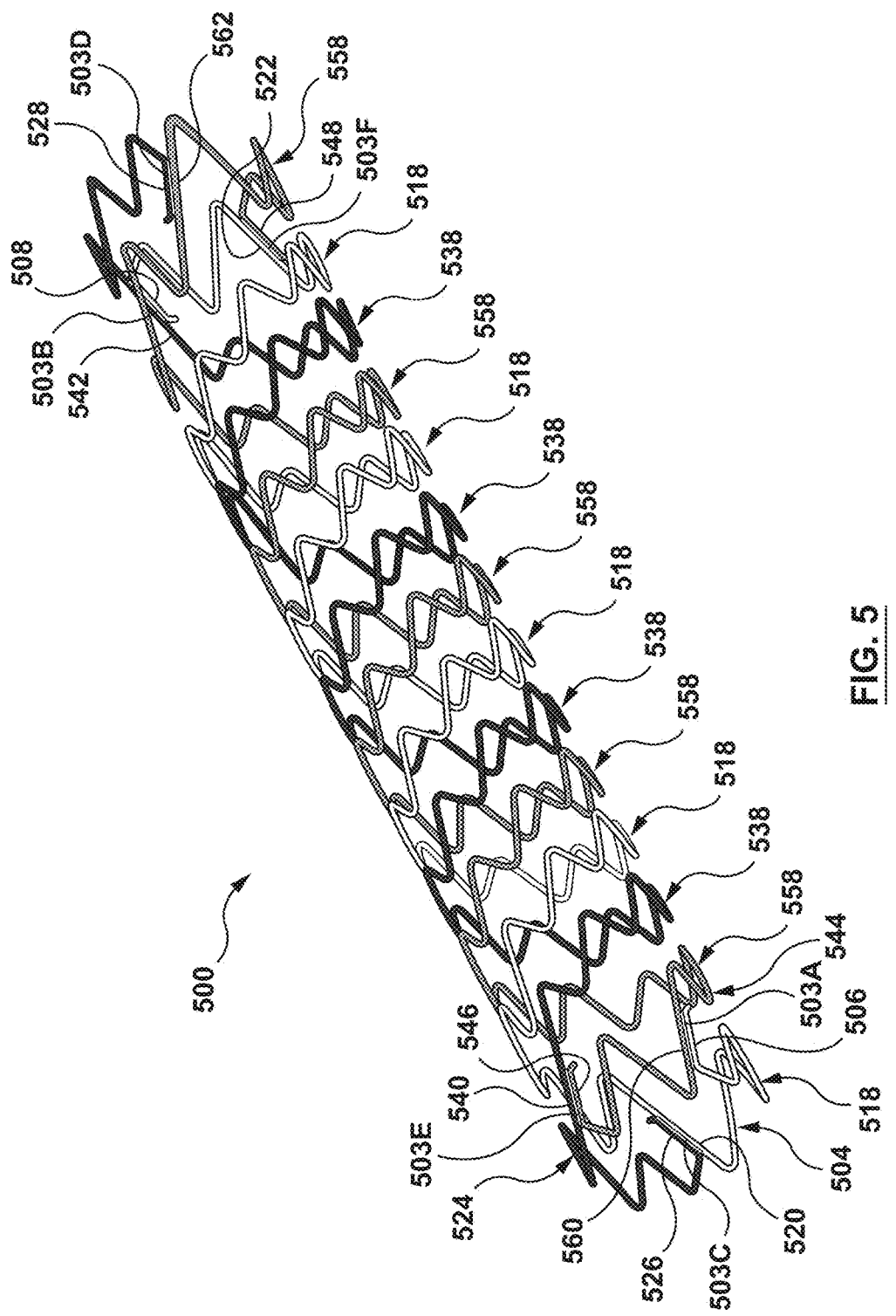
FIG. 5 is a perspective view of a stent prosthesis according to an embodiment hereof, wherein the stent prosthesis includes a first wire bent into a first waveform and spirally wrapped into a first helix having a plurality of windings, a second wire bent into a second waveform and spirally wrapped into a second helix having a plurality of windings, and a third wire bent into a third waveform and spirally wrapped into a third helix having a plurality of windings.

Although FIGS. 1 and 4 illustrate prostheses having only first and second wires 104, 124, it will be understood by one of ordinary skill in the art that more than two wires may be utilized in stent prosthesis 100 and stent-graft prosthesis 400. An embodiment of a stent prosthesis is shown in FIG. 5 that includes first, second, and third wires that are each spirally wrapped into a helix but other multiples of wires beyond three are contemplated. More particularly, FIG. 5 is a perspective view of a stent prosthesis 500 that includes a first wire 504 bent into a first waveform and spirally wrapped into a first helix having a plurality of windings 518, a second wire 524 bent into a second waveform and spirally wrapped into a second helix having a plurality of windings 538, and a third wire 544 bent into a third waveform and spirally wrapped into a third helix having a plurality of windings 558. In FIG. 5, first, second, and third wires 504, 524, 544 are shown with varying degrees of shading for sake of illustration only in order to distinguish first, second, and third wires 504, 524, 544 from each other. First, second, and third wires 504, 524, 544 are disposed relative to each other such that the plurality of windings 518, 538, 558 of each of the first, second, and third wires 504, 524, 544 are disposed about a common longitudinal axis, i.e., longitudinal axis $L_4$, and are axially offset from each other. First, second, and third wires 504, 524, 544 are axially offset from each other by being spirally wrapped at differing starting points into a hollow cylindrical shape. Windings 518 of first wire 504, windings 538 of second wire 524, and windings 558 of third wire 544 alternate between each other such that windings 518, 538, 558 of first, second, and third wires 504, 524, 544, respectively, occur in or form a repeating series or pattern. Stated another way, windings 518 of first wire 504, windings 538 of second wire 524, and windings 558 of third wire 544 are intertwined, interlaced, or interwoven with each other such that along midportions of first, second, and third wires 504, 524, 544 a single winding 518 of the first helix (formed by first wire 504) is disposed between a single winding 538 of the second helix (formed by second wire 524) and a single winding 558 of the third helix (formed by third wire 544). Further, a single winding 538 of the second helix is disposed between a single winding 518 of the first helix and a single winding 558 of the third helix. Still further, a single winding 558 of the third helix is disposed between a single winding 538 of the second helix and a single winding 518 of the first helix.

Similar to embodiments described above, first, second, and third wires 504, 524, 544 are independent or separate from each other and are not attached to each other at least along midportions thereof. However, the free ends of first wire 504 are attached to third wire 544, the free ends of second wire 524 are attached to first wire 504, and the free ends of third wire 544 are attached to second wire 524 in order to provide additional strength and stability to stent prosthesis 500. More particularly, as shown in FIG. 5, first end 506 of first wire 504 is attached or secured to a first elongated strut 560 of third wire 544 via a weld 503A or connector (not shown) and second end 508 of first wire 504 is attached or secured to a second elongated strut 542 of second wire 524 via a weld 503B or connector (not shown). Similarly, first end 526 of second wire 524 is attached or secured to a first elongated strut 520 of first wire 504 via a weld 503C or connector (not shown) and second end 528 of second wire 524 is attached or secured to a second elongated strut 562 of third wire 544 via a weld 503D or connector (not shown). Similarly, first end 546 of third wire 544 is attached or secured to a first elongated strut 540 of second wire 524 via a weld 503E or connector (not shown) and second end 548 of third wire 544 is attached or secured to a second elongated strut 522 of first wire 504 via a weld 503F or connector (not shown). In an embodiment, first elongated strut 520 and second elongated strut 522 are disposed at opposing end portions of first wire 504, first elongated strut 540 and second elongated strut 542 are disposed at opposing end portions of second wire 524, and first elongated strut 560 and second elongated strut 562 are disposed at opposing end portions of third wire 544. Utilization of elongated struts as an attachment point between first, second, and third wires 504, 524, 544 is beneficial because such elongated struts permit longer lengths of welds 503A, 503B, 503C, 503D, 503E, 503F. Longer welds ensure that the structural strength of stent prosthesis 500 is not adversely compromised as described above with respect to welds 103A, 103B, 103C, 103D.

However, although struts 540, 542, 520, 522, 560, 562 are illustrated and described as elongated, in another embodiment hereof these struts may have a length equal to the length of other struts of the respective waveform and thus are not required to be elongated as described above. In addition, although first, second, and third wires 504, 524, 544 are illustrated and described with only struts 540, 542, 520, 522, 560, 562 as being elongated compared to the vast majority of struts of the respective waveform, in another embodiment hereof additional struts may alternatively and/or additionally be elongated. Further, although such additional elongated struts are not required to be utilized in an attachment point between two wires of prosthesis 500, such additional elongated struts may be utilized in the formation of additional attachments points between a pair of wires in order to provide further strength and stability to stent prosthesis 500. For example, in an embodiment hereof, additional attachments points between first, second, and third wires 504, 524, 544 may be desired along midportions thereof when stent prosthesis 500 is a relatively longer prosthesis. As the length-diameter aspect ratio of stent prosthesis 500 increases, additional attachment points between first, second, and third wires 504, 524, 544 may be desired along midportions thereof.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A stent-graft prosthesis comprising:
 a tubular graft;

a first wire bent into a first waveform and spirally wrapped into a first helix having a plurality of windings that form a hollow cylindrical shape, the first wire having opposing first and second ends and a midportion extending therebetween, wherein the first wire is coupled to the tubular graft; and a second wire bent into a second waveform and spirally wrapped into a second helix having a plurality of windings that form a hollow cylindrical shape, the second wire having opposing first and second ends and a midportion extending therebetween, wherein the second wire is coupled to the tubular graft, wherein the first and second wires are disposed relative to each other such that the plurality of windings of the first wire and the plurality of windings of the second wire are disposed about a common longitudinal axis and the plurality of windings of the first wire and the plurality of windings of the second wire are axially offset from each other, with windings of the plurality of windings of the first wire interwoven between windings of the plurality of windings of the second wire along a length of the stent-graft prosthesis, wherein each of the first and second waveforms of the first and second wires, respectively, have a generally sinusoidal configuration with a plurality of crowns and a plurality of struts with each crown being formed between a pair of opposing struts, and wherein the first and second wires are not coupled to each other along at least the midportions thereof except through the tubular graft, and wherein the first end of the first wire is attached to a first strut of the second waveform of the second wire via a first elongated attachment component and the first end of the second wire is attached to a first strut of the first waveform of the first wire via a second elongated attachment component.

2. The stent-graft prosthesis of claim 1, wherein the first strut of the second waveform of the second wire is an elongated strut and the first strut of the first waveform of the first wire is an elongated strut.

3. The stent-graft prosthesis of claim 2, wherein the second end of the first wire is attached to a second strut of the second waveform of the second wire and the second end of the second wire is attached to a second strut of the first waveform of the first wire.

4. The stent-graft prosthesis of claim 2, wherein the first wire and the second wire have an equal diameter and a length of each of the first and second elongated attachment components is four times the equal diameter of the first and second wires.

5. The stent-graft prosthesis of claim 1, wherein the first helix has the same pitch and diameter as the second helix.

6. The stent-graft prosthesis of claim 1, wherein each of the first and second elongated attachment components is a weld.

7. The stent-graft prosthesis of claim 6, wherein each of the first wire and the second wire are formed from a superelastic material.

8. A stent-graft prosthesis comprising:
a tubular graft;
a first wire bent into a first waveform and spirally wrapped into a first helix having a plurality of windings that form a hollow cylindrical shape, the first wire having opposing first and second ends and a midportion extending therebetween, wherein the first wire is coupled to the tubular graft; and a second wire bent into a second waveform and spirally wrapped into a second helix having a plurality of windings that form a hollow cylindrical shape, the second wire having opposing first and second ends and a midportion extending therebetween, wherein the second wire is coupled to the tubular graft, wherein the first and second wires are disposed relative to each other such that the plurality of windings of the first wire and the plurality of windings of the second wire are disposed about a common longitudinal axis and the plurality of windings of the first wire and the plurality of windings of the second wire are axially offset from each other, with windings of the plurality of windings of the first wire interwoven between windings of the plurality of windings of the second wire along a length of the stent-graft prosthesis, wherein the first and second wires are not coupled to each other except through the tubular graft.

9. The stent-graft prosthesis of claim 8, further comprising:

a third wire bent into a third waveform and spirally wrapped into a third helix having a plurality of windings that form a hollow cylindrical shape, wherein the third wire is disposed such that the plurality of windings of the third wire are also disposed about the common longitudinal axis and the plurality of windings of the third wire are axially offset from the pluralities of windings of the first and second wires, with windings of the pluralities of windings of the first, second, and third wires interwoven between each other.

10. The stent-graft prosthesis of claim 8, wherein each of the first and second waveforms of the first and second wires, respectively, have a generally sinusoidal configuration.

11. The stent-graft prosthesis of claim 8, wherein the first helix has the same pitch and diameter as the second helix.

12. A stent-graft prosthesis comprising:
a tubular graft;
a first wire bent into a first waveform and spirally wrapped into a first helix having a plurality of windings that form a hollow cylindrical shape, the first wire having opposing first and second ends and a midportion extending therebetween, wherein the first wire is coupled to the tubular graft;

a second wire bent into a second waveform and spirally wrapped into a second helix having a plurality of windings that form a hollow cylindrical shape, the second wire having opposing first and second ends and a midportion extending therebetween, wherein the second wire is coupled to the tubular graft; and a third wire bent into a third waveform and spirally wrapped into a third helix having a plurality of windings that form a hollow cylindrical shape, the third wire having opposing first and second ends and a midportion extending therebetween, wherein the third wire is coupled to the tubular graft, wherein each of the first, second, and third waveforms of the first, second, and third wires, respectively, have a generally sinusoidal configuration with a plurality of crowns and a plurality of struts with each crown being formed between a pair of opposing struts, wherein the first, second, and third wires are disposed relative to each other such that the plurality of windings of each of the first, second, and third wires are disposed about a common longitudinal axis and the plurality of windings of each of the first, second, and third wires are axially offset from each other, with windings of the pluralities of windings of the first, second, and third wires interwoven between each other along a length of the prosthesis, wherein the first, second, and third wires are not coupled to each other along at least the midportions thereof except through the tubular graft, and wherein the first end of the first wire is attached to a first strut of the third waveform of the third wire via a first elongated attachment component, the first end of the second wire is attached to a first strut of the first waveform of the first wire via a second elongated attachment component, and the first end of the third wire is attached to a first strut of the second waveform of the second wire via a third elongated attachment component.

13. The stent-graft prosthesis of claim 12, wherein the first strut of the third waveform of the third wire is an elongated strut, the first strut of the first waveform of the first wire is an elongated strut, and the first strut of the second waveform of the second wire is an elongated strut.

14. The stent-graft prosthesis of claim 12, wherein the second end of the first wire is attached to a second strut of the second waveform of the second wire, the second end of the second wire is attached to a second strut of the third waveform of the third wire, and the second end of the third wire is attached to a second strut of the first waveform of the first wire.

15. The stent-graft prosthesis of claim 12, wherein the first, second, and third helices each have the same pitch and diameter.

16. The stent-graft prosthesis of claim 12, wherein each of the first, second, and third elongated attachment components is a weld.

\* \* \* \* \*